United States Patent
Bewick-Sonntag et al.

(10) Patent No.: US 8,329,979 B2
(45) Date of Patent: Dec. 11, 2012

(54) SIMPLIFIED ABSORBENT PAD

(75) Inventors: Christopher Phillip Bewick-Sonntag, Cincinnati, OH (US); Thomas Ward Osborn, III, Cincinnati, OH (US)

(73) Assignee: The Procter and Gamble Company, Cincinnati, OH (US)

(*) Notice: Subject to any disclaimer, the term of this patent is extended or adjusted under 35 U.S.C. 154(b) by 1882 days.

(21) Appl. No.: 10/422,670

(22) Filed: Sep. 8, 2003

(65) Prior Publication Data
US 2004/0044319 A1 Mar. 4, 2004

Related U.S. Application Data

(63) Continuation-in-part of application No. 09/905,804, filed on Jul. 13, 2001, now abandoned, which is a continuation-in-part of application No. 09/637,400, filed on Aug. 11, 2000, now Pat. No. 6,635,799.

(51) Int. Cl.
*A61F 13/15* (2006.01)

(52) U.S. Cl. ........................................ 604/378; 604/383

(58) Field of Classification Search .................. 604/378, 604/381–384
See application file for complete search history.

(56) References Cited

U.S. PATENT DOCUMENTS

| | | | |
|---|---|---|---|
| 3,783,196 A | 1/1974 | Stanley | |
| 3,903,890 A * | 9/1975 | Mesek et al. | 604/365 |
| 3,996,389 A | 12/1976 | Osborn | |
| 4,021,503 A | 5/1977 | Goulding | |
| 4,031,427 A | 6/1977 | Stanley | |
| 4,175,561 A | 11/1979 | Hirschman | |
| 4,886,632 A | 12/1989 | Van Iten | |
| 5,137,600 A | 8/1992 | Barnes | |
| H1376 H | 11/1994 | Osborn | |
| 5,399,175 A * | 3/1995 | Glaug et al. | 604/385.101 |
| 5,403,300 A | 4/1995 | Howarth | |
| 5,414,914 A | 5/1995 | Suzuki | |
| 5,470,326 A * | 11/1995 | Dabi et al. | 604/383 |
| 5,611,790 A | 3/1997 | Osborn, III | |
| 5,643,588 A * | 7/1997 | Roe et al. | 424/402 |
| 5,762,641 A | 6/1998 | Bewick-Sonntag | |
| 5,785,697 A * | 7/1998 | Trombetta et al. | 604/378 |
| 5,836,929 A | 11/1998 | Bewick-Sonntag | |
| 5,873,867 A | 2/1999 | Coles | |
| 5,904,971 A * | 5/1999 | Anderson et al. | 428/112 |
| 5,968,026 A | 10/1999 | Osborn et al. | |
| 5,998,695 A | 12/1999 | Roe | |
| 6,022,818 A | 2/2000 | Welchel | |
| 6,066,388 A | 5/2000 | Van Kerrebrouck | |
| 6,103,952 A | 8/2000 | Coles | |
| 6,152,905 A | 11/2000 | Osborn, III | |
| 6,232,521 B1 | 5/2001 | Bewick-Sonntag | |

FOREIGN PATENT DOCUMENTS

FR 2703244 10/1994

(Continued)

*Primary Examiner* — Lynne Anderson
(74) *Attorney, Agent, or Firm* — Andres E. Velarde; Amanda T. Barry (57) ABSTRACT

An absorbent pad having a periphery and useful as a feminine hygiene article. The pad comprises a body-contacting surface comprising fibers from a first web of fibrous material, an absorbent portion comprising fibers from a second web of fibrous material, and a bottom surface comprising fibers from the first web of fibrous material. The absorbent portion is disposed intermediate the body-contacting surface and the bottom surface and extends to the periphery, the surfaces and absorbent portion being joined to one another at portions of the first web that penetrate through the absorbent portion at a plurality of discrete locations.

31 Claims, 3 Drawing Sheets

FOREIGN PATENT DOCUMENTS

| | | |
|---|---|---|
| WO | WO 95/16424 A1 | 6/1995 |
| WO | WO 95/17869 A1 | 7/1995 |
| WO | WO 95/17870 A1 | 7/1995 |
| WO | WO 97/01996 A1 | 1/1997 |
| WO | WO 99/55265 A1 | 11/1999 |
| WO | WO 99/55272 A1 | 11/1999 |
| WO | WO 99/56689 A1 | 11/1999 |
| WO | WO 00/38604 A1 | 7/2000 |

* cited by examiner

SIMPLIFIED ABSORBENT PAD

CROSS REFERENCE TO RELATED APPLICATIONS

This is a continuation in part of application Ser. No. 09/905,804 filed on Jul. 13, 2001, now abandoned, which was a continuation in part of application Ser. No. 09/637,440 filed on Aug. 11, 2000, now U.S. Pat. No. 6,635,799.

FIELD OF INVENTION

The present invention relates to absorbent pads. Specifically, this invention relates to disposable absorbent pads for absorbing fluids such as body exudates.

BACKGROUND OF THE INVENTION

Disposable absorbent articles such as sanitary napkins and pantiliners are known. Typically such disposable absorbent articles have a fluid permeable body-side liner called a topsheet, a fluid impermeable garment-side liner called a backsheet, and an absorbent core disposed between the topsheet and the backsheet in a layered relationship.

Disposable absorbent articles having the basic design described above also comprise such devices as disposable diapers, adult incontinence pads and devices, pull-up training pants, and the like. Other components such as tape tabs, side tabs (i.e., "wings"), panty adhesives, release strips, and the like, but the basic necessary structure remains: a topsheet, a core, and a backsheet in a layered relationship. This structure requires, at minimum, three materials to be provided to a process for making disposable absorbent articles. Topsheet and backsheet materials are typically provided as roll stock and fed into a converting process as continuous webs of material. Absorbent cores can likewise be provided in the form of a continuous web, or provided as discrete core members by known methods.

In known methods, therefore, converting lines in which webs of materials are converted into finished products at commercial line speeds can be very complex as each of the components must be precisely placed, joined (e.g., via adhesive bonding) and cut at high speeds. The complexity of the process limits product production rates, thereby contributing to higher product costs.

Furthermore, each layer, e.g., topsheet, core, and backsheet, adds a degree of stiffness to the finished product. The stiffness of each component is compounded in the finished article due to the necessary addition of adhesives to join together the necessary component. While certain articles, such as sanitary napkins and pantiliners benefit from increased flexibility, the adhesives necessary to join the various components of such catamenial pads often render the pads relatively stiff and uncomfortable.

Accordingly, it would be desirable to have a more flexible absorbent pad, such as a feminine hygiene pad, including catamenial pads, such as sanitary napkins or pantiliners.

Further, it would be desirable to have a simplified pad construction such that the number of component layers is reduced.

Finally, it would be desirable to have a simplified pad having no adhesive present to combine the component layers.

SUMMARY OF THE INVENTION

An absorbent pad having a periphery and useful as a feminine hygiene article is disclosed. The pad comprises a body-contacting surface comprising fibers from a first web of fibrous material, an absorbent portion comprising fibers from a second web of fibrous material, and a bottom surface comprising fibers from the first web of fibrous material. The absorbent portion is disposed intermediate the body-contacting surface and the bottom surface and extends to the periphery, the surfaces and absorbent portion being joined to one another at portions of the first web that penetrate through the absorbent portion at a plurality of discrete locations.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

The invention is disclosed for use as a feminine hygiene article, such as a urinary incontinence device or a catamenial pad (e.g., a sanitary napkin or pantiliner). However, the invention is not limited to such a use. The structure of the pad can be useful for many varied uses, such as for use as cleaning pads, filter pads, disposable diapers, incontinence products, hemorrhoid treatment pads, or any other use in which soft, absorbent pads are beneficial.

Figure 1:
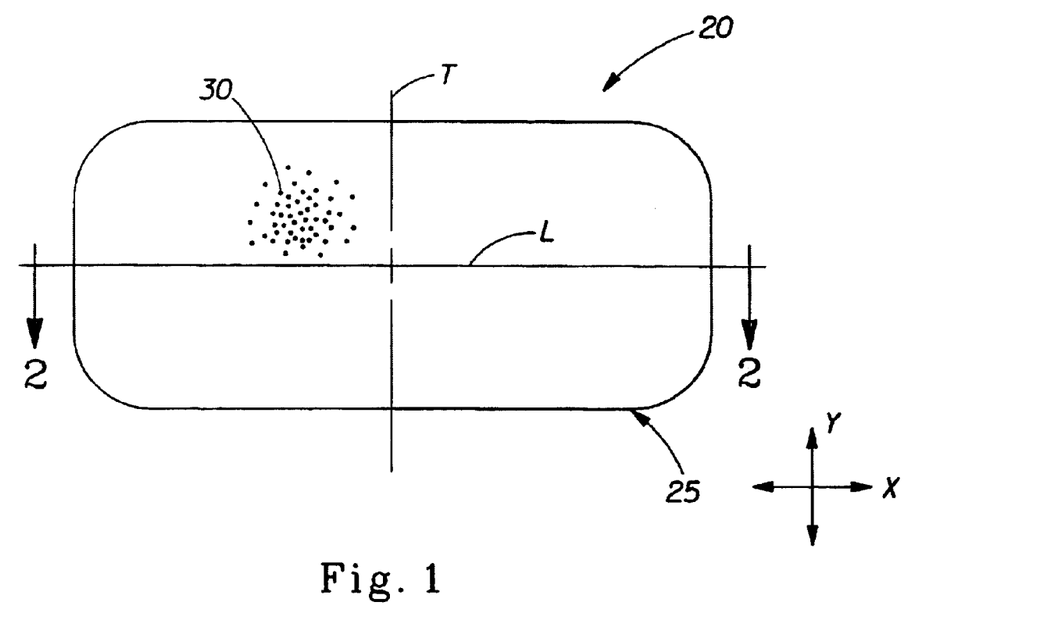
FIG. 1 is a plan view of a pad of the present invention.
Figure 2:
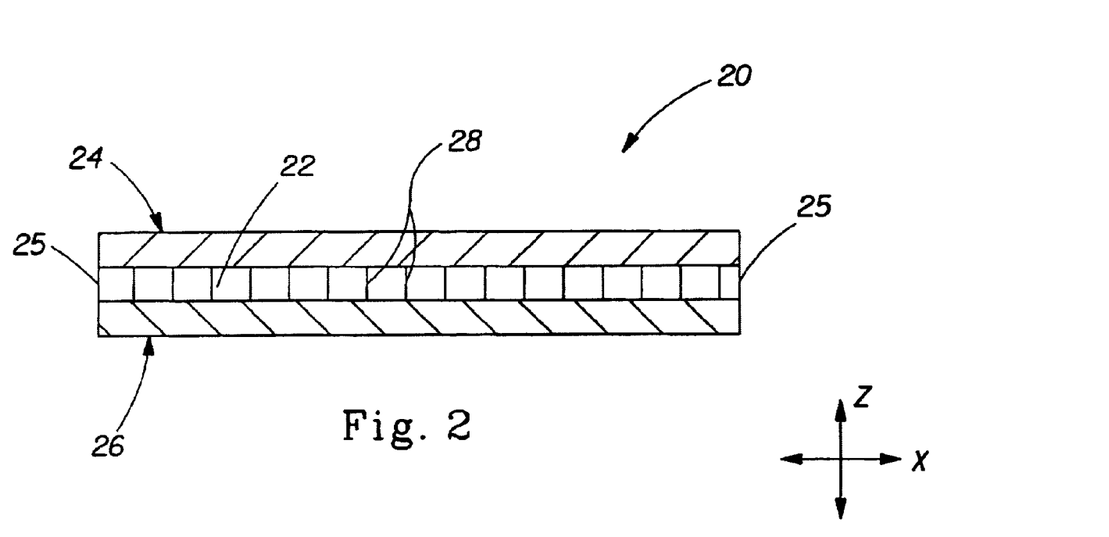
FIG. 2 is a cross-sectional view of the pad shown in FIG. 1.

The pad 20 shown in FIG. 1 has a longitudinal centerline L. The term "longitudinal", as used herein, refers to a line, axis or direction in the plane of the pad 20 that is aligned with the longest dimension of the pad 20. For sanitary napkins the term refers to an axis or direction in the plane of the pad 20 that is generally aligned with (e.g., approximately parallel to) a vertical plane which bisects a standing wearer into left and right body halves when the pad 20 is worn. The pad 20 shown in FIG. 1 also has a transverse centerline T. The terms "transverse," "lateral," as used herein, are interchangeable, and refer to a line, axis, or direction that is generally perpendicular to the longitudinal axis. The pad 20 also has an axis in the "z" direction, which is perpendicular to the plane defined by the longitudinal and transverse centerlines (i.e., the x-y plane), and generally corresponds to the direction associated with the thickness (sometimes referred to as "caliper") dimension of pad 20. The shape of pad 20 is defined by peripheral edge 25.

The pad 20 as shown in FIGS. 1-4 has a first surface, which can be a top surface, and is described herein as a body-facing (or "body-contacting") side 24, and an opposed bottom surface or underside 26. The pad comprises a absorbent portion 22. The pad 20 can be in any suitable shape. Non-limiting examples of shapes for the absorbent pad 20 when viewed from the top as in FIG. 1 include round (in which case, of course, "longitudinal" and "transverse" would be arbitrary), ovoid, elliptical, trapezoidal, rectangular, triangular, or diamond-shaped.

To increase the wearing comfort of the pad 20, it is preferably flexible enough to fold easily and conform about the anatomy of a wearer, for example, the pudendal region of a female wearer.

The pad 20 preferably has sufficient absorbency to absorb and retain fluids, such as body exudates, e.g., blood, urine menses or rectal leakage, discharged from the wearer's body. While actual capacity requirements can be negligible, it is desirable that the pad 20 have some absorbent capacity. The absorbent capacity is dependent at least partially upon the physical size, i.e., volume, of the pad 20.

The size of the pad 20 can be important to its comfort and effectiveness when used as a feminine hygiene pad. The length of the pad 20 is the maximum dimension measured parallel to the longitudinal centerline L in the longitudinal direction. The width of the pad 20 is the maximum dimension measured parallel to the transverse centerline T in the transverse direction. The thickness (or caliper) is the maximum "z"-direction dimension of the pad 20. Caliper measurements given herein were measured using an AMES gauge with a 0.25 psi (1.7 kPa) (gauge) load and a 0.96 inch (2.44 cm) diameter foot. Those skilled in the art will recognize that if a 0.96 inch (2.44 cm) diameter foot is not appropriate for a particular sample size, the foot size may be varied while the load on the gauge is accordingly varied to maintain a confining pressure of 0.25 psi (1.7 kPa) (gauge).

The pad 20 of the present invention can have a liquid capacity sufficient to absorb moderate amounts of vaginal discharge, including menses and/or urine. Preferably, the pad 20 has sufficient capacity to absorb at least about 0.2 gram of vaginal discharge, more preferably of at least about 1.0 gram, and most preferably of at least about 5.0 grams. The absorbent portion 22 can have a total capacity of at least about 10.0 grams. In general the absorbent capacity can be chosen according to the end use requirement of the pad.

The pad 20 preferably has a capacity of at least about 0.1 g of 0.9% by weight saline solution, and may have a capacity of up to about 350 g by using absorbent gels or foams that expand when wet. Preferably, for pads used interlabially capacities typically range from about 2 to about 10 grams, for saline. Those skilled in the art will recognize that the capacity for absorption of vaginal discharges such as menses will typically be smaller than the capacities given above for absorption of saline. A method for measuring absorbent capacity is by way of the Absorbent Capacity Test Method is disclosed in the Test Methods section, below.

Table 1 below summarizes the preferred dimensions and absorbent capacities for specific applications of pad 20. For each of the parameters disclosed as a range herein, the disclosure is hereby intended to also disclose at least whole number intervals within the range. For example, in the range 4-13 cm it is recognized that 5 cm, 6 cm, 7 cm . . . and 12 cm, is fully and completely described therein.

TABLE 1

Typical Dimensions for Pad 20

| Product Application | Length (cm) | Width (cm) | Caliper (mm) | Absorbent Capacity (grams) |
|---|---|---|---|---|
| Hemorrhoid/Interlabial Pad | 4-13 | 3-7 | 1-4 | 0.1-10 |
| Pantiliner (vaginal discharges, urine) | 5-22 | 1-7 | 1-4 | 0.1-100 |
| Light-Moderate Incontinence Pad | 14-38 | 2-15 | 2-9 | 50-350 |
| Catamenial Pad | 14-35 | 4-10 | 2-7 | 10-70 |
| Personal Cleaning pad | 6-20 | 4-15 | 1-4 | <30 |

Figure 3:
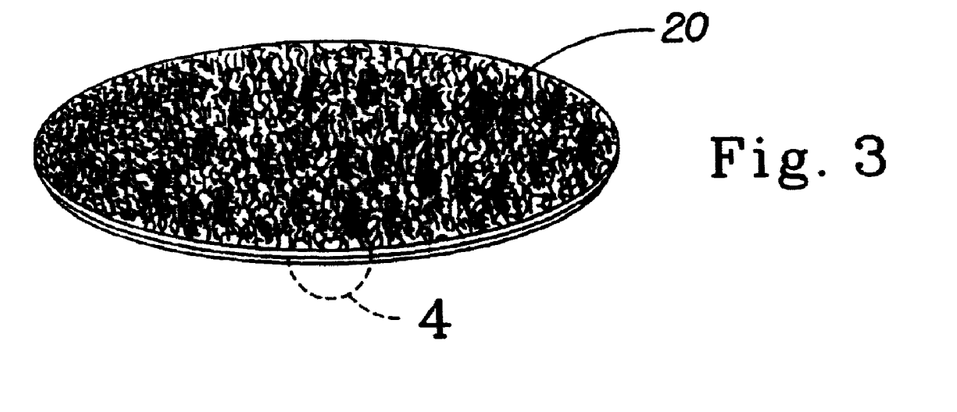
FIG. 3 is a perspective view of a pad of the present invention.
Figure 4:
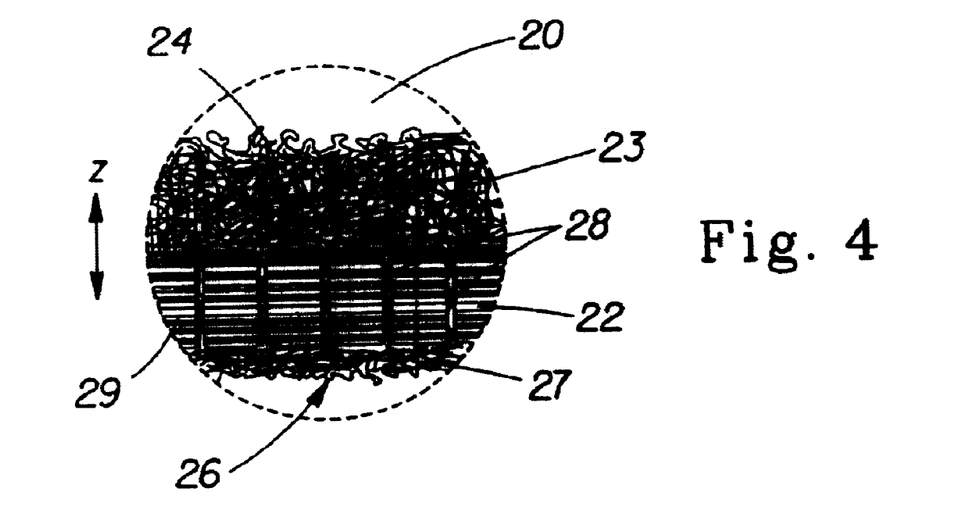
FIG. 4 is an enlarged cross-sectional view of a portion of the pad shown in FIG. 3.

As shown in FIGS. 3 and 4, a simplified pad of the present invention is simplified in at least two ways: (1) pad 20 is in a sense a "three layer" pad made from only two starting webs or materials (sometimes referred to as precursor webs), and, (2) pad 20 is die-cut to shape, without the need for a seam or other bonding means about periphery 25. With respect to the "layers," pad 20 has a comprises a first layer 23 comprising body-contacting surface 24 and a second layer 27 comprising bottom surface 26, both the first and second layers comprised of the same material, and both having originated from the same precursor nonwoven web, as described more fully below, and a third layer 29 comprising an absorbent portion 22 disposed intermediate the first layer and second layer and certain of the fibers from body-contacting surface 24 which extend through absorbent portion 22 via fiber channels 28 to bottom surface 26. This structure results in an integral pad in which three layers are formed from only two starting webs, and all the layers are joined without the need for adhesives or other bonding means. Integration and formation of the fiber channels 28 can be achieved by needle-punching by methods known in the art.

The body-contacting surface 24 and bottom surface 26 are each a fibrous surface made by needle punching a relatively loosely bonded fibrous nonwoven web through an absorbent layer to form an integral pad that includes the body-contacting surface 24 that serves the purpose of a topsheet as is typically known in the art of sanitary napkins, for example, and a bottom surface 26 which serves the purpose of the garment-facing surface of a sanitary napkin, for example. The body-contacting surface 24 and bottom surface 26 can be made from a precursor nonwoven web having a basis weight of about 30-300 grams per meter squared (gsm) and having sufficient fiber lengths and sufficiently low inter-fiber bonding so as to permit fibers to be needle punched through the absorbent portion 22 and to extend through absorbent portion 22 in a sufficient quantity to form bottom surface 26. In general, and specifically for use as a feminine hygiene article, a sufficient quantity of fibers to form bottom surface 26 is a quantity to give the bottom surface the appearance of being comprised of a uniform nonwoven web. A sufficient quantity can be achieved by choosing a sufficiently closely-spaced density of needles in a needle punching apparatus, and a sufficient "draw" or stroke of the needles, both parameters being selected and implemented by means well known by those skilled in the art.

In a preferred embodiment for use as a light incontinence pad device, the precursor nonwoven web can be a web of staple or carded fibers, the web having a basis weight of from about 50-180 gsm, and more preferably 60 to 120 gsm. The precursor nonwoven web can have a caliper of between about 2-10 mm when measured under 7.0 grams per square meter (0.1 psi) pressure. The fibers of the precursor nonwoven web are preferably carded fibers having a length of less than about 38 mm, and preferably between about 25-80 mm, and can be between about 2-8 denier, preferably less than about 4 denier.

In one non-limiting example, precursor web for body-contacting surface 24 and bottom surface 26 can be a 60 gsm carded nonwoven layer comprised of a mixture of bi-component fibers and Tencel rayon fibers. In a preferred version of this embodiment, the body-contacting surface 24 and bottom surface 26 comprises about 50% by weight KoSa type #T255 bi-component fibers obtained from KoSa, (Charlotte, N.C.) and about 50% by weight of a 38 mm, 3 denier Lyocel fiber with a standard medical finish and obtained from Tencel Ltd. (Grimsby, U.K).

In another non-limiting example, precursor web for body-contacting surface 24 and bottom surface 26 can comprise a hi-loft web manufactured in either a long fiber airlaid process or a carded process. For example a web suitable for converting into body-contacting surface 24 and bottom surface 26 can be manufactured by airlaying a blend of staple fibers having a length of approximately 8-20 mm, the blend comprising about 10-25% bi-component binding fibers. For example a fiber blend of 40% by weight KoSa type #T255 bi-component fibers obtained from KoSa, (Charlotte, N.C.), 40% 12 mm long, 1.75 denier Lyocel available from Tencel Ltd. (Grimsby, UK) and 20% 8 mm long, bi-component fiber (8 mm, C1.7 dtex, AL Adhesion) available from FiberVisions Covington, Ga., USA can be airlaid either onto forming screen or another substrate such as the absorbent portion 22.

In another non-limiting example, precursor web for body-contacting surface 24 and bottom surface 26 can be a 60 gsm carded nonwoven layer comprised of a blend of 40% by weight hydrophilic conventional tri-lobal 3 denier GALAXY® rayon containing 0.01% by weight LEOMIN® (known in Europe as ASLAN®) hydrophobic finish (which can also serve as a processing aid), and 60% by weight hydrophobically-treated conventional tri-lobal 3 denier GALAXY® rayon containing 0.03% by weight LEOMIN® finish, both fibers supplied by Acordis Ltd. (Grimsby, UK).

In another non-limiting example, body-contacting surface 24 and bottom surface 26 can be a 60 gsm carded nonwoven layer comprised of a blend of 40% by weight hydrophilic conventional tri-lobal 3 denier GALAXY® rayon containing 0.01% LEOMIN® finish supplied by Acordis Ltd. (Grimsby, UK), and 60% by weight BIONELLE 3001® biodegradable fibers obtained from Showa Hugh Polymer Co. of Tokyo, Japan or fibers that provide equivalent biodegradable performance.

The absorbent portion 22 may comprise any suitable material that is capable of absorbing and/or retaining liquids (e.g. blood) and can be made by traditional needle-punching or by use of a spiked roll arrangement as is known in the art. The absorbent portion 22 can be manufactured from a wide variety of liquid-absorbent materials commonly used in absorbent articles such as comminuted wood pulp which is generally referred to as airfelt. Examples of other suitable absorbent materials include cotton fibers or cotton lintels, creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers (in fibrous and particulate form); absorbent gelling materials; or any equivalent material or combinations of materials, or mixtures of these. The absorbent portion 22 may comprise a single material or a combination of materials.

In a preferred embodiment, the absorbent portion 22 can comprise fibrous superabsorbent material in any suitable amount. Alternatively, instead of comprising fibrous superabsorbent material, in a less preferred embodiment, the super absorbent material can be in the form of particles, or any other form known in the art. In other embodiments, the absorbent portion 22 can comprise superabsorbent material in a combination of different forms. Further, a fibrous absorbent portion can comprise the fibrous gelling materials from the group consisting of: chitosan, alginates, and cross-linked starch.

In one embodiment, the absorbent portion 22 comprises a 200 g/m$^2$ airlaid layer comprised of superabsorbent fibers, airfelt, and bicomponent fibers. Although the superabsorbent fibers can be distributed in any suitable manner within the absorbent core, the superabsorbent fibers are preferably distributed substantially uniformly throughout the absorbent portion 22. The absorbent portion 22 can comprise a high concentration (greater than or equal to about 25% by weight but typically less than 70% by weight) of a fibrous superabsorbent material (or absorbent gelling material), preferably a high gel strength fibrous superabsorbent material to avoid the phenomena of gel blocking or loss of gelling material at the product edges.

In another embodiment a more selective blood gelling material class of compounds such as Chitosan fibers or Chitosan doped cellulose fibers can be chosen either with or in substitution of fibrous gelling material to more selectively gel and bind blood based bodily discharges.

The layers of pad 20, i.e., body-contacting surface 24, absorbent portion 22, and bottom surface 26 are integrally formed by needle-punching a precursor nonwoven web through a fibrous absorbent web, such as a web of fibrous absorbent gelling materials. Such a structure is disclosed in U.S. patent application Ser. No. 09/905,804, which is hereby incorporated herein by reference. This application published Feb. 21, 2002 as WO 02/13750.

In addition to the simplified construction afforded by simply needle punching two base precursor webs into a three-layered absorbent structure, pad 20 can be additionally simplified for use as a feminine hygiene product by cutting out of the needlepunched three-layer structure a shaped pad. Cutting can be by any means known in the art, including by hand, by use of lasers, or other means known in the art. In a more commonly used commercially-viable process cutting can be achieved by rotary die cutting as is known in the art. Such rotary-die-cut pads 20 can then be used "as-is" for light incontinence by placing the pad into the crotch region of the wearer's panties. That is, the pad of the present invention can be useful without requiring that the pad be sealed about its periphery, or be used as one of many components in a complete article, as disclosed in the above-mentioned WO 02/13750. If necessary, attachment adhesives, commonly referred to as panty fastening means as known in the art can be added to aid in holding pad 20 in place for use as a catamenial device.

Cutting the pad to shape as disclosed herein results in a layered structure in which the absorbent portion 22 extends completely to the peripheral edge 25. It is recognized that simple cutting to shape, without simultaneously crimping or heat sealing the periphery 25, and without any additional sealing processes, results in an absorbent portion that extends to and is exposed at the periphery 25 of pad 20 which remains unsealed at the periphery 25. However, for many uses, such as for light adult incontinence, such a pad may be sufficient. Furthermore, potential leakage of absorbed fluids can be minimized or avoided by treating the pad 20 with suitable treatments, such as a hydrophobic substance treatment to the periphery 25 of pad 20 such that fluids are hindered from being absorbed or otherwise transferred to periphery 25. For example, hydrophobic treatments such as a hydrophobic lotion comprising petrolatum can be applied on body-facing surface 24 of pad 20 to block the passage of urine out of pad 20. In another embodiment a silicone based agent may be applied to the pad perimeter. In addition to serving to restrict passage of urine out of the pad edge, hydrophobic treatments of the pad perimeter also serve to restrict swelling of absorbent gelling materials (AGM) at the pad perimeter that could result in AGM being squeezed out at the pad edge. In another approach a solution of a multivalent ion may be applied to the pad edge to effectively quench the AGM's absorption properties, thereby inhibiting the movement of fluid to the periphery of pad 20.

For better protection against soiling when pad 20 is used as a catamenial device, bottom surface 26 can be rendered at least partially fluid impermeable. In a preferred embodiment In a preferred embodiment, bottom surface 26 is rendered liquid impermeable (although it may remain breathable, by means known in the art with respect to breathable films). By liquid impermeable is meant that when loaded by a uniform distribution of liquid to 50% capacity and then pressed at 0.25 psi pressure onto a Watman® 40 filter paper for 15 minutes, not more than 2 grams of liquid is absorbed by the Watman® filter paper. In one embodiment, bottom surface 26 can be rendered liquid impermeable by adhering thereto an impermeable polymer film, such as a polyethylene film, which is commonly referred to as a backsheet in the art of sanitary napkins.

In another embodiment, bottom surface 26 can be rendered at least partially liquid impermeable by the application of a curable liquid resin, such as a latex resin that, once cured, fills and blocks the interstices between fibers of bottom surface 26. In a preferred embodiment, the curable liquid resin does not appreciably add to the stiffness of pad 20 when cured.

In another embodiment, a panty applied adhesive design that essentially covers a significant proportion of the product dimensions may be chosen to provide both the desired level of fluid impermeable barrier as well as the required panty fastening capability.

In another embodiment, bottom surface 26 can be rendered at least partially liquid impermeable by the application of heat from a heat source sufficient to re-flow and melt bond adjacent bondable fibers in bottom surface 26. Application of heat can be by means known in the art, such as by radiant heat, heated surfaces, e.g., heated rollers, hot wire contact, and other such means of applying localized heat. The advantage of re-flowing the polymer of the fibers in bottom surface 26 is that no additional materials need be added to make a fully functional catamenial device, such as a sanitary napkin. That is, using terminology common in the art of sanitary napkins, the body-contacting surface 24 serves as the fluid permeable "topsheet" and the bottom surface as the fluid impermeable "backsheet" with the absorbent portion, i.e., an absorbent "core" disposed therebetween. Other optional components such as panty adhesive, "wings" and the like can be added as desired.

It is recognized that in some cutting operations the periphery 25 of pad 20 may be sealed incidentally. For example, if pads 20 are cut by laser cutting the laser may incidentally at least partially seal about the periphery of pad 20. Likewise, if cutting is by heated die cutting means, the heated dies may adhere the periphery of pad 20.

The pad 20 can have a substance 30 deposited on the body-side surface 24 prior to use, the substance 30 being capable of providing comfort or skin treatment benefits. When used as a sanitary napkin, for example, a skin treatment lotion can be provides as substance 30, such as a petrolatum-based lotion that can be transferred to the skin of the wearer. The presence of the substance 30 should not interfere with the flushability or biodegradability of the pad 20.

Suitable non-adhesive substances 30 include waxes (such as microcrystalline waxes, paraffinic waxes, silicone waxes, polyethylene waxes), fatty alcohols, high molecular weight alcohols, fatty acids, petroleum jelly, sealing ointments, non-ionic surfactants such as ethoxylated alcohols, ethoxylated long chain alcohols, and ethoxylated fatty acids, alkoxylated amide, alkoxylated amines, alkyl amido alkyl amines, alkyl substituted amino acids, moisture-activated substances, and combinations thereof.

A substance 30 for holding the pad 20 in place can be combined with other substances before it is applied to the pad. Such other substances can serve as a component of the substance 30, or as a carrier for the substance 30. Non-limiting examples of substances that can serve in either of these manners are lotions, emollients, and mineral oil. For example, the substance 30 can be a polyethylene glycol that is mixed in a lotion formula that provides lubricity. In another example, an emollient can be used as a carrier for PEG's which are in particulate form. In still another example, the PEG's can be in liquid form, and can serve as a carrier for other materials.

The substance 30 described above can be applied to the body-contacting surface of the pad 20 in an intermittent pattern, a continuous pattern, or in a pattern that has both intermittent and non-uniform portions. By "intermittent" it is meant that the amount, location, pattern of distribution, etc. of the lotion composition can vary over the topsheet surface. For example, some portions of the treated surface of the topsheet can have greater or lesser amounts of lotion composition, including portions of the surface that do not have any lotion composition on it. Applying the substances in an intermittent pattern, such as in a longitudinally-oriented stripe (or stripes), may be useful if it is desired to minimize interference of the substances with acquisition of liquids into the pad 20 since liquids can be transported into the absorbent portion 22 between the intermittent zones of the substance. Applying the substances in a continuous pattern may be useful if it is desired to use the contact that the substance 30 makes to the wearer's body to create a barrier to the flow of exudates over the body-contacting surface of the pad. However, the application of the substances in a continuous pattern should not form an impermeable barrier which prevents rectal discharges, blood, or feces from being absorbed by the pad 20.

Where the substance 30 is applied intermittently, any pattern may be utilized, including, for example, application of small droplets (obtained via, e.g., spraying or printing) discrete dots (obtained via, e.g., gravure printing or ink jet printing), alternating stripes that run in the longitudinal or lateral direction of the article, etc. By alternating stripes is meant regions in which the lotion is applied as stripes separated by regions which have no lotion applied. The substance 30 can be applied directly to the pad 20, or it may be applied to another material or component which is then adhered to the desired portion of the pad 20. The substance 30 can cover any of the following percentages of the surface area of the body-contacting surface of the absorbent portion 22, the central absorbent portion, the flexible extensions, or the entire body-contacting surface of the pad In those embodiments where the body-contacting surface of the absorbent portion 22, comprises discrete, untreated regions, the percent open area of the region of the body-contacting surface can vary widely. (As referred to herein, the "percent open area" of the body-contacting surface is determined by (i) measuring the surface area of the body-contacting surface, (ii) measuring the total surface area of the untreated region(s) of the body-contacting surface and (iii) dividing the measurement in (ii) by the measurement in (i). As used herein, "untreated" means a region of the body-contacting surface having less than about 0.05 g/m$^2$ of substance 30. In this regard, the percent open area may be from about 1% to about 99%, from about 5% to about 95%, from about 10% to about 90%, from about 15% to about 85%, from about 20% to about 80%, from about 25% to about 75%, from about 30% to about 70%, or from about 35% to about 65%. The percent open area required to achieve the desired substance 30 effect and the desired fluid handling properties of the topsheet will be dictated largely by the characteristics of the substance 30 (in particular the lotion's composition and its relative hydrophobicity/hydrophilicy properties).

For certain lotion compositions (e.g., those that are hydrophobic), the untreated regions of body-contacting surface 24 further facilitate passage of fluids into the absorbent portion 22. While the body-contacting surface 24 is treated intermittently (e.g., the body-contacting surface 24 has microscopic or macroscopic regions where no lotion is applied), during wear of the article, lotion is transferred to the wearer even in regions of the skin corresponding to non-lotion regions of the body-contacting surface 24. The amount and uniformity of lotion transferred to the skin is believed to depend on several factors, including, for example, contact of the wearer's skin to the topsheet, friction created during wear time between the wearer's skin and the treated topsheet, warmth generated from wearer to enhance the transfer of the lotion, the lotion properties, lotion composition, and the like.

In one preferred embodiment of a catamenial product, the body-contacting surface 24 comprises stripes of lotion that run in the article's longitudinal direction. In such embodiments, each lotion stripe can typically have a width of from about 1.0 mm to about 24.0 mm, more typically from about 1.0 mm to about 12 mm, and the width of the stripes containing no lotion can typically be from about 1.0 mm to about 24 mm, more typically from about 1.0 mm to about 12 mm.

The substance 30 can be applied to the pad 20 in any suitable quantity. For these purposes, the quantity of the substance 30 applied to the pad 20 can be expressed as a percentage of the total product weight including the pad and the weight of the substance 30. Preferably, the substance 30 constitutes less than or equal to about 20%, more preferably less than or equal to about 10%, and most preferably less than or equal to about 5% of the total product weight, so as not to excessively contribute to the overall weight of the pad. This permits more of the total product weight to be dedicated to providing absorbent capacity.

Alternatively, the quantity of the substance 30 applied to the pad 20 can be expressed as an amount applied to the body contacting surface 24. Preferably, the substance 30 can be applied from about 0.0155 g/m$^2$ (0.01 mg/in$^2$) to about 310 g/m$^2$ (200 mg/in$^2$) preferably from about 0.155 g/m$^2$ (0.1 mg/in$^2$) to about 155 g/m$^2$ (100 mg/in$^2$), more preferably 0.5 g/m$^2$ (0.32 mg/in$^2$) to about 93 g/m$^2$ (60 mg/in$^2$), to the absorbent article. Of course, for articles having relatively high percent open areas in the body contacting surface, greater add-on levels may be obtainable without adversely affecting the pad 20.

The pad 20 can be provided with various optional features. For example, the pad 20 of the present invention can provide a benefit to the user in controlling odors associated with body exudates by adding odor controlling agents to, for example, the absorbent portion 22. Such odor controlling agents include, but are not limited to activated charcoals, zeolites, silica, polyacrylic acids (superabsorbents), certain quaternary compounds, triethyl citrate, cyclodextrin, or any combinations thereof. Particularly preferred cyclodextrin compounds are described in U.S. Pat. No. 5,429,628 issued to Trihn, et al. and U.S. Pat. No. 5,780,020 issued to Peterson, et al. In addition, deodorants can be added to further mask these odors.

Further, other substances 30 can be added to the body contacting surface 24 for one or more of the following purposes: cleansing, providing soothing and refreshing effects, deodorizing, relieving minor irritation, reducing the number of pathogenic microorganisms, or producing an astringent effect.

Preferably, the pad 20 of the present invention is toilet-disposable. The term "toilet-disposable", as used herein, means that the pad is capable of being disposed of in a toilet, i.e., the pad is at least flushable. In particularly preferred embodiments, the pad may also be disintegrateable and/or biodegradable.

As used herein, the terms "flushable" and "flushability" refer to a product's ability to pass though typically commercially available household toilets and plumbing drainage systems without causing clogging or similar problems that can be directly associated with the physical structure of the product. It is recognized, however, that there can be many differences between the various types of toilets available. Flushability is measured according to the Flushability Test described below.

Disintegrateability and biodegradability can be measured in accordance with the 28 Day Sludge Test which is in the Test Methods section below. Preferably, the pad 20 comprises biodegradable materials. While biodegradable materials are preferred for the pad 20, it is not necessary that each and every material used be biodegradable. For example, the pad 20 may comprise superabsorbent particles which do not biodegrade, and this will not affect the ability of the overall pad 20 to remain toilet-disposable and to be effectively processed in a sewage treatment system. On an overall weight basis, the pad 20 is preferably at least about 70% biodegradable, more preferably at least about 80% biodegradable, more preferably still at least about 90% biodegradable, and most preferably, at least about 95% biodegradable.

Test Methods

Unless otherwise noted, all of the methods are conducted under the standard laboratory climatic control as specified by TAPPI under T402 om-93, Section 3 (73° F. or 23° C.±1° C., 50%±2% RH). All samples should be acclimated to these conditions for two hours prior to measurements.

Absorbent Capacity Test

The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and laid horizontally on a wire mesh screen having square openings 0.25 inches by 0.25 inches (0.64 cm by 0.64 cm) for five minutes to allow the saline to drain out to the article. Both sides of the article are then covered with absorbent blotters, such as the filter paper #631 available from the Filtration Science Corp., Eaton-Dikeman Division of Mount Holly Springs, Pa. A uniform 1 pound per square inch (6.9 Pa) load is placed over the article to squeeze excess fluid out. The absorbent blotters are replaced every 30 seconds until the amount of fluid transferred to the absorbent blotters is less than 0.5 grams in a 30 second period. Next, the article is weighed to the nearest 0.1 gram and the dry weight of the article is subtracted. The difference in grams is the absorbent capacity of the article.

Flushability Test

Overview

As noted above, the terms "flushable" or "flushability" refer to a product's capacity to pass through typical commercially available household toilets and plumbing drainage systems without causing clogging or similar problems that can be directly associated with the physical characteristics of the product. The flushability test procedure is designed to simulate two days of normal toilet usage for a family of 4 (2 men, 2 women). The test employs a flushing sequence to simulate the following conditions: male urination visits, female urination visits (including post urinary drying with tissue), disposal of the product (that is, the interlabial device or other device to be tested) with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 5:
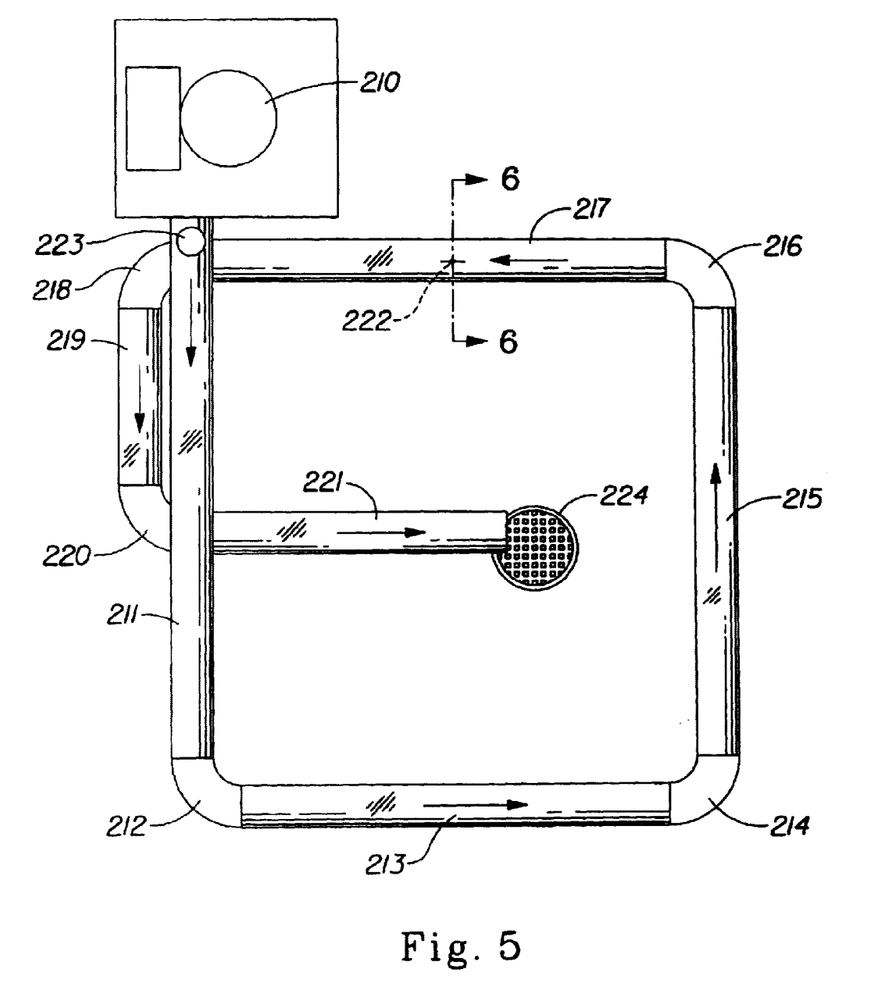
FIG. 5 is a schematic representation of an apparatus suitable for a flushability test.
Figure 6:
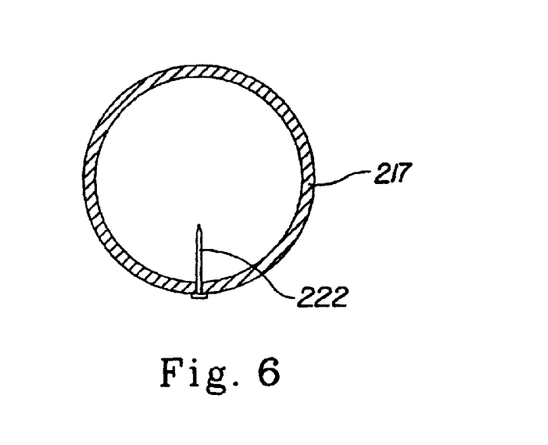
FIG. 6 is a cross-sectional representation of a portion of the apparatus shown in FIG. 5.

An apparatus suitable for the flushability test is shown in plan view in FIG. 5. The apparatus includes:
- a 3.5 gallon (13.2 liter) water saver siphon vortex toilet referred to as 210 (additional toilets can also be attached to the piping layout shown in FIG. 17 to evaluate the behavior of test samples using different flushing mechanisms such as commercial, pressure toilets);
- approximately 59 feet (18 meters) of 4 inch (10 cm) inside diameter acrylic pipe (As can be seen from FIG. 17, the piping is assembled in roughly a square configuration having linear runs 211, 213, 215, 217, 219, 221 approximately 10 feet (3 meters) long);
- a cast iron tee 223 slightly downstream of the toilet 210 that is open to the atmosphere for venting;
- five cast iron ninety degree elbows 212, 214, 216, 218, and 220;
- a snag 222 positioned vertically (FIG. 6) approximately 15 feet from the pipe's terminal end and approximately 1 inch (2.5 cm) long; and
- a screen (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: "CHARMIN" toilet tissue manufactured by The Procter & Gamble Company of Cincinnati, Ohio.

Synthetic Fecal Material: Prepared according to the method described below.

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and the product to be tested and 6 flushes with tissue and simulated fecal matter (SFM). When it is used, the SFM is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips (or the catamenial product) are placed in the bowl at 10 second intervals. Ten seconds after the final strip or product is placed into the bowl, the toilet is flushed. The flushing sequence is described below as a series of two routines combined in the following order:

Routine #1 (To be performed first 6 times for a total of 30 flushes)
1) Flush With Tissue Only—Take a drain line blockage reading 2 minutes after the water reaches the simulated obstruction, wait 1 additional minute, and move to step 2.
2) Flush With Empty Bowl. Take a drain line blockage reading 2 minutes after the water reaches the snag point and move to step 3.
3) Flush With Tissue and Product—Take a drain line blockage reading 2 minutes after the water reaches the snag point, wait 1 additional minute, and move to step 4.
4) Flush With Empty Bowl. Take a drain line blockage reading 2 minutes after the water reaches the snag point and move to step 5.
5) Flush With Tissue and Simulated Fecal Matter (SFM). Take a drain line blockage reading 2 minutes after the water reaches the snag point, wait 1 additional minute.

Routine #2 (To be performed 1 time)
1) Flush With Tissue Only—Take a drain line blockage reading 2 minutes after the water reaches the snag point, wait 1 additional minute, and move to step 2.
2) Flush With Empty Bowl. Take a drain line blockage reading 2 minutes after the water reaches the snag point and move to step 3.
3) Flush With Tissue Only—Take a drain line blockage reading 2 minutes after the water reaches the snag point, wait 1 additional minute, and move to step 4.
4) Flush With Empty Bowl. Take a drain line blockage reading 2 minutes after the water reaches the snag point.

Total number of flushes per sequence is 34.

If, after the second flush in the flushing sequence, the product remains in the bowl or trap after flushing, the tissue and or product is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:
1) Incidence of failure (%) of the product to clear bowl and trap in one flush
2) Incidence of failure (%) of the product to clear bowl and trap in two flushes
3) Incidence of product on simulated snag
4) Maximum level (%) of drain line blockage 5) Cumulative level (%) of drain line blockage over the 2 day simulated test period.

By flushable as used herein is meant that the products described herein will completely clear the bowl at least about 70% of the time in two or fewer flushes, more preferably at least about 80% of the time in one flush, even more preferably at least about 90% of the time in one flush, and most preferably at least about 95% of the time in one flush. The products described herein will preferably have a maximum level of drain line blockage of less than or equal to about 80%. The products described herein will preferably have a cumulative level of drain line blockage over the 2 day simulated test period of less than or equal to about 50%.

Preparation of Synthetic Fecal Material

I. Materials Needed:
  Feclone synthetic fecal matter (900 grams);
  (Available from Siliclone Studio, Valley Forge, Pa. as product BFPS-7 dry concentrate)
  Tap water at 1000° C. (6066 grams)

II. Equipment Needed:
  Mixer (Available from Hobart Corp., Troy, Ohio as Model A200)
  Extruder (Available from Hobart Corp., Troy, Ohio as Model 4812)
  Disposable Centrifuge tubes with screw caps (50 ml) (Available from VWR Scientific, Chicago, Ill. as Catalog No. 21-008-176)
  Water Bath to control temperature to 37° C.

III. Preparation:
  1. Pour the 100° C. water into the mixing bowl of the mixer and add the dry Feclone concentrate.
  2. Mix on low for 1 minute.
  3. Mix on medium speed for 2 minutes.
  4. After the material is well mixed, transfer to the extruder.
  5. Using an ice pick, punch a small hole in the tip of each centrifuge tube.
  6. Extrude the Feclone into the centrifuge tubes.
  7. Cap the centrifuge tubes and store in the refrigerator.
  8. Before using, put the tubes in the water bath at 38° C.

28 Day Sludge Test

Purpose:

To determine the extent to which an absorbent article disintegrates upon exposure to biologically active anaerobic sludge. Anaerobic conditions are typically found in household septic tanks, as well as in municipal sewage treatment facilities in the form of anaerobic sludge digesters. Test products, such as the absorbent article are combined with anaerobic digester sludge to determine the extent and rate of disintegration of test products over a 28 day period. Disintegration (as measured by weight change) is typically measured on days 3, 7 14, 21 and 28 of the particular study. This protocol is modeled after the National Sanitation Foundation, Ann Arbor, Mich., International Protocol: Evaluation of the Anaerobic Disintegration of a Test Product, November, 1992.

Materials:

Control Product

TAMPAX Regular brand tampons are used as a positive control product in the anaerobic disintegration test.

Material Preparation

Prior to the addition of the test and control products to the reactors, the materials will be dried in a hot air oven at 103°±0±2° C. for 2 hours and then weighed to determine the initial weight. Approximately equal weights of the control and test products will be placed in respective reactors.

Anaerobic Sludge:

The sludge used in this evaluation will be anaerobic sludge obtained from a municipal waste water treatment plant, or raw sewage obtained as influent from a waste water treatment plant that has been concentrated by settling and decanting the overlying water. Prior to use in the evaluation, the following parameters of the sludge will be measured in accordance with standard laboratory operating procedures:
  Total solids
  Total volatile solids
  pH The sludge should meet the following criteria for use in the evaluation:
  pH between 6.5 and 8
  Total solids≧15,000 mg/L
  Total volatile solids≧10,000 mg/L The criteria for the activity of the sludge requires that the control tampon material must lose at least 95% of its initial dry weight after 28 days exposure.

Procedure:

The test and control products are added to an appropriately sized glass flask (reactor) containing an appropriate volume of anaerobic digester sludge or concentrated raw sewage. For products of less than 50 sq cm area a 2 L wide mouth glass flask (reactor) containing 1500 ml of anaerobic digester sludge or concentrated raw sewage is chosen. For products between 51 and 100 sq cm area a 4 L wide mouth glass flask and 3000 ml of anaerobic digester sludge or concentrated raw sewage are chosen. The glass flask size and sludge/sewage levels are doubled for every 50 sq cm interval in product area as shown above. Three reactor flasks per test material per sampling day are prepared. Thus, if disintegration is measured on days 3, 7, 14, 21, and 28, there will be a total of 15 reactor flasks for the test product and 15 flasks for the control product. The reactors are sealed and placed in an incubator maintained at 35±2° C. On the specified sampling days, three reactors each for the test and control material are removed from the incubator. On the designated sample days, the contents of each reactor will be passed through a 1 mm mesh screen to recover any undisintegrated material. Any collected material will be rinsed with tap water, removed from the screen and placed in a hot air oven at 103±2° C. for at least 2 hours. The dried material will be weighed to determine final weight. Visual observations of the physical appearance of the materials when recovered from the reactors will also be made and recorded.

Results:

The rate and extent of anaerobic disintegration of each test material and the control material is determined from initial dry weights of the material and the dried weights of the material recovered on the sampling days. The percent anaerobic disintegration is determined using the following equation (percent weight loss):

Percent Disintegration=(initial dry weight−final dry weight)×100(initial dry weight)

The average percent disintegration for the test and control products for each sampling day will be presented. For the purposes of the appended claims, the percent disintegration values are for day 28 of the study.

What is claimed is:

1. An absorbent pad having a periphery and formed from a first web of fibrous material and a second web of fibrous material, the absorbent pad comprising:
  a. a top surface consisting essentially of a first layer, the first layer consisting essentially of fibers from the first web of fibrous material;

b. a bottom surface consisting essentially of a second layer, the second layer consisting essentially of fibers from the first web of fibrous material;
c. a third layer comprising an absorbent portion comprising fibers from the second web of fibrous material; and wherein,
d. the absorbent portion is disposed intermediate the first layer and the second layer and extends to the periphery, the first and second layers and absorbent portion being joined to one another at portions of the first web that penetrate through the absorbent portion at a plurality of discrete locations.

2. The absorbent pad of claim 1, wherein the absorbent portion is adapted to absorb blood and has an absorbent capacity of at least 0.10 grams when tested according to the Absorbent Capacity Test.

3. The absorbent pad of claim 1, wherein the first and second layers and absorbent portion being joined to one another by needle punching.

4. The absorbent pad of claim 1, wherein the first web is an airlaid web.

5. The absorbent pad of claim 1, wherein the absorbent portion comprises fibrous absorbent gelling materials.

6. The absorbent pad of claim 1, further comprising a substance disposed on the top surface.

7. The absorbent pad of claim 6, wherein the substance is applied intermittently.

8. The absorbent pad of claim 6, wherein the substance is a petrolatum-based lotion.

9. The absorbent pad of claim 1, wherein the bottom surface is rendered at least partially fluid impermeable.

10. The absorbent pad of claim 1, wherein the first and second layers and absorbent portion are joined to one another only at the portions of the first web that penetrate through the absorbent portion at the plurality of discrete locations.

11. An absorbent pad having a periphery and formed from a first web of fibrous material and a second web of fibrous material, the absorbent pad consisting of:
   a. a top surface consisting essentially of a first layer, the first layer consisting essentially of fibers from the first web of fibrous material;
   b. a bottom surface consisting essentially of a second layer, the second layer consisting essentially of fibers from the first web of fibrous material;
   c. a third layer comprising an absorbent portion having an absorbent capacity of at least about 5 grams when tested according to the Absorbent Capacity Test and comprising fibers from the second web of fibrous material; and wherein,
   d. the absorbent portion is disposed intermediate the first layer and the second layer and extends to the periphery, the first and second layers and absorbent portion being joined to one another at portions of the first web that penetrate through the absorbent portion at a plurality of discrete locations.

12. The absorbent pad of claim 11, wherein the first and second layers and absorbent portion being joined to one another by needle punching.

13. The absorbent pad of claim 11, wherein the first web is an airlaid web.

14. The absorbent pad of claim 11, wherein the absorbent portion comprises fibrous absorbent gelling materials.

15. The absorbent pad of claim 11, further comprising a substance disposed on the body-contacting surface.

16. The absorbent pad of claim 15, wherein the substance is applied intermittently.

17. The absorbent pad of claim 15, wherein the substance is a petrolatum-based lotion.

18. The absorbent pad of claim 14, wherein the absorbent portion further comprises fibrous gelling materials from the group consisting of chitosan, alginates, and cross-linked starch.

19. The absorbent pad of claim 11, further comprising a fluid impermeable backsheet joined to the bottom surface.

20. The absorbent pad of claim 11, wherein the first and second layers and absorbent portion are joined to one another only by the portions of the first web that penetrate through the absorbent portion at the plurality of discrete locations.

21. A sanitary napkin having a periphery and formed from a first web of fibrous material and a second web of fibrous material, the sanitary napkin comprising:
   a. a fluid permeable body-contacting surface consisting essentially of fibers from the first web of fibrous material;
   b. an absorbent portion having an absorbent capacity of at least about 5 grams when tested according to the Absorbent Capacity Test and comprising fibers from the second web of fibrous material;
   c. a fluid impermeable bottom surface consisting essentially of fibers from the first web of fibrous material; and wherein,
   d. the absorbent portion is disposed intermediate the body-contacting surface and the bottom surface and extends to the periphery, the surfaces and absorbent portion being joined to one another at portions of the first web that penetrate through the absorbent portion at a plurality of discrete locations.

22. The sanitary napkin of claim 21, wherein the surfaces and absorbent portion being joined to one another by needle punching.

23. The sanitary napkin of claim 21, wherein the first web is an airlaid web.

24. The absorbent pad of claim 21, wherein the absorbent portion comprises fibrous absorbent gelling materials.

25. The sanitary napkin of claim 21, further comprising a substance disposed on the body-contacting surface.

26. The sanitary napkin of claim 25, wherein the substance is applied intermittently.

27. The sanitary napkin of claim 25, wherein the substance is a petrolatum-based lotion.

28. The sanitary napkin of claim 21, further comprising a fluid impermeable backsheet joined to the bottom surface.

29. The sanitary napkin of claim 21, wherein the surfaces and absorbent portion are joined to one another only by the portions of the first web that penetrate through the absorbent portion at the plurality of discrete locations.

30. The sanitary napkin of claim 21, wherein the sanitary napkin has an average percent disintegration of at least about 70% when tested by the 28 Day Sludge Test.

31. The sanitary napkin of claim 21, wherein the sanitary napkin is flushable by clearing the bowl at least about 70% of the time in two or fewer flushes, as tested by the Flushability Test.

* * * * *